(12) United States Patent
Corley

(10) Patent No.: US 9,302,034 B2
(45) Date of Patent: Apr. 5, 2016

(54) NEGATIVE PRESSURE WOUND THERAPY DRESSING

(75) Inventor: Kevin Corley, Reading, MA (US)

(73) Assignee: Smith & Nephew, Inc., Memphis, TN (US)

(*) Notice: Subject to any disclaimer, the term of this patent is extended or adjusted under 35 U.S.C. 154(b) by 266 days.

(21) Appl. No.: 14/110,120

(22) PCT Filed: Mar. 28, 2012

(86) PCT No.: PCT/US2012/030829
§ 371 (c)(1),
(2), (4) Date: Dec. 18, 2013

(87) PCT Pub. No.: WO2012/138514
PCT Pub. Date: Oct. 11, 2012

(65) Prior Publication Data
US 2014/0094761 A1 Apr. 3, 2014

Related U.S. Application Data

(63) Continuation-in-part of application No. 13/079,298, filed on Apr. 4, 2011, now abandoned.

(51) Int. Cl.
*A61M 1/00* (2006.01)
*A61F 13/02* (2006.01)
*A61F 13/00* (2006.01)

(52) U.S. Cl.
CPC ........ *A61M 1/0088* (2013.01); *A61F 13/00068* (2013.01); *A61F 13/0203* (2013.01);
(Continued)

(58) Field of Classification Search
USPC ........................................................ 604/319
See application file for complete search history.

(56) References Cited

U.S. PATENT DOCUMENTS

| 3,026,874 A | 3/1962 | Stevens |
| 3,367,332 A | 2/1968 | Groves |

(Continued)

FOREIGN PATENT DOCUMENTS

| DE | 41 11 122 A1 | 4/1993 |
| DE | 43 06 478 | 9/1994 |

(Continued)

OTHER PUBLICATIONS

U.S. Appl. No. 13/775,964, filed Feb. 25, 2013, Haggstrom et al.
(Continued)

*Primary Examiner* — Adam Marcetich
*Assistant Examiner* — Guy K Townsend
(74) *Attorney, Agent, or Firm* — Knobbe, Martens, Olson & Bear LLP

(57) ABSTRACT

A wound dressing suitable for use in negative pressure wound therapy system includes a cover layer adapted to establish a reservoir over a wound in which a negative pressure may be maintained. The cover layer includes an opening therein through which atmospheric gasses and wound exudates may pass through the cover layer. A vacuum port is affixed to the cover layer, and establishes a substantially fluid tight seal about the opening in the cover layer. The vacuum port includes a hollow interior in fluid communication with the opening in the cover layer and a connector to facilitate connection to a vacuum source. A packing member is affixed to the cover layer, to provide a wound dressing that may be applied in a single step process. The packing member is adapted to fill the wound and support the cover layer when a negative pressure is applied to the reservoir.

18 Claims, 4 Drawing Sheets

(52) U.S. Cl.
CPC .......... *A61M1/0086* (2014.02); *A61M 1/0096* (2014.02); *A61F 2013/0074* (2013.01); *A61F 2013/00174* (2013.01)

(56) References Cited

U.S. PATENT DOCUMENTS

| | | | |
|---|---|---|---|
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,202,331 A | 5/1980 | Yale |
| 4,224,945 A | 9/1980 | Cohen |
| 4,228,798 A | 10/1980 | Deaton |
| 4,266,545 A | 5/1981 | Moss |
| 4,280,680 A | 7/1981 | Payne |
| 4,382,441 A | 5/1983 | Svedman |
| 4,422,293 A | 12/1983 | Ewald |
| 4,510,802 A | 4/1985 | Peters |
| 4,524,064 A | 6/1985 | Nambu |
| 4,538,645 A | 9/1985 | Perach |
| 4,655,754 A | 4/1987 | Richmond et al. |
| 4,665,909 A | 5/1987 | Trainor |
| 4,700,479 A | 10/1987 | Saito et al. |
| 4,710,165 A | 12/1987 | McNeil et al. |
| 4,738,257 A | 4/1988 | Meyer et al. |
| 4,743,232 A | 5/1988 | Kruger |
| 4,870,975 A | 10/1989 | Cronk et al. |
| 4,874,363 A | 10/1989 | Abell |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,135,485 A | 8/1992 | Cohen et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,180,375 A | 1/1993 | Feibus |
| 5,195,977 A | 3/1993 | Pollitt |
| 5,261,893 A | 11/1993 | Zamierowski |
| 5,263,922 A | 11/1993 | Sova et al. |
| 5,399,418 A | 3/1995 | Hartmanns et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,624,374 A | 4/1997 | Von Iderstein |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,779,657 A | 7/1998 | Daneshvar |
| 5,840,049 A | 11/1998 | Tumey et al. |
| 5,899,871 A | 5/1999 | Cartmell et al. |
| 5,911,222 A | 6/1999 | Lawrence et al. |
| 5,928,174 A | 7/1999 | Gibbins |
| 5,944,703 A | 8/1999 | Dixon et al. |
| 5,960,837 A | 10/1999 | Cude |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Turney et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Byordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |

(56) References Cited

U.S. PATENT DOCUMENTS

| | | |
|---|---|---|
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,524,315 B2 | 4/2009 | Blott et al. |
| 7,569,742 B2 | 8/2009 | Haggstrom et al. |
| 7,699,823 B2 | 4/2010 | Haggstrom et al. |
| 7,708,724 B2 | 5/2010 | Weston |
| 7,838,717 B2 | 11/2010 | Haggstrom et al. |
| 7,846,141 B2 | 12/2010 | Weston |
| 7,964,766 B2 | 6/2011 | Blott et al. |
| 8,062,272 B2 | 11/2011 | Weston |
| 8,207,392 B2 | 6/2012 | Haggstrom et al. |
| 8,257,327 B2 | 9/2012 | Blott et al. |
| 8,409,157 B2 | 4/2013 | Haggstrom et al. |
| 8,444,612 B2 | 5/2013 | Patel et al. |
| 8,777,911 B2* | 7/2014 | Heagle et al. ............... 604/317 |
| 2001/0020145 A1 | 9/2001 | Satterfield et al. |
| 2001/0029956 A1* | 10/2001 | Argenta et al. ............... 128/897 |
| 2001/0031943 A1 | 10/2001 | Urie |
| 2001/0043943 A1 | 11/2001 | Coffey |
| 2002/0016577 A1 | 2/2002 | Ohmstede |
| 2002/0108614 A1 | 8/2002 | Schultz |
| 2002/0143286 A1 | 10/2002 | Tumey |
| 2002/0151836 A1 | 10/2002 | Burden |
| 2002/0161346 A1 | 10/2002 | Lockwood et al. |
| 2002/0198503 A1* | 12/2002 | Risk et al. ............... 604/315 |
| 2002/0198504 A1* | 12/2002 | Risk et al. ............... 604/318 |
| 2003/0078532 A1 | 4/2003 | Ruszczak et al. |
| 2003/0093041 A1 | 5/2003 | Risk, Jr. et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risk, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0039742 A1 | 2/2006 | Cable et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz et al. |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0078432 A1 | 4/2007 | Halseth et al. |
| 2007/0129707 A1 | 6/2007 | Blott et al. |
| 2007/0161938 A1 | 7/2007 | Aali |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0219513 A1 | 9/2007 | Lina et al. |
| 2007/0225663 A1 | 9/2007 | Watt et al. |
| 2007/0233022 A1 | 10/2007 | Henley et al. |
| 2008/0009812 A1 | 1/2008 | Riesinger |
| 2008/0011667 A1 | 1/2008 | Ruschke |
| 2008/0071235 A1 | 3/2008 | Locke et al. |
| 2008/0082059 A1 | 4/2008 | Fink et al. |
| 2008/0103462 A1 | 5/2008 | Wenzel et al. |
| 2008/0132819 A1 | 6/2008 | Radl et al. |
| 2008/0134796 A1 | 6/2008 | Clerc et al. |
| 2008/0167593 A1 | 7/2008 | Fleischmann |
| 2008/0183233 A1 | 7/2008 | Koch et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2009/0012483 A1* | 1/2009 | Blott et al. ............... 604/315 |
| 2009/0054855 A1* | 2/2009 | Blott et al. ............... 604/290 |
| 2009/0306580 A1* | 12/2009 | Blott et al. ............... 604/22 |
| 2010/0036334 A1 | 2/2010 | Heagle et al. |
| 2010/0256545 A1* | 10/2010 | Aali et al. ............... 602/43 |
| 2010/0286635 A1 | 11/2010 | Watson, Jr. |
| 2011/0028918 A1 | 2/2011 | Hartwell |
| 2011/0054421 A1 | 3/2011 | Hartwell |
| 2011/0172615 A2 | 7/2011 | Greener |
| 2011/0213287 A1 | 9/2011 | Lattimore et al. |
| 2012/0253302 A1 | 10/2012 | Corley |
| 2013/0138060 A1 | 5/2013 | Haggstrom et al. |
| 2013/0144230 A1* | 6/2013 | Wu et al. ............... 604/319 |
| 2013/0204213 A1* | 8/2013 | Heagle et al. ............... 604/304 |
| 2014/0094761 A1* | 4/2014 | Corley ............... 604/319 |

FOREIGN PATENT DOCUMENTS

| | | |
|---|---|---|
| DE | 295 04 378 U1 | 10/1995 |
| EP | 358 302 | 3/1990 |
| EP | 1 088 569 | 4/2001 |
| EP | 1 219 311 | 7/2002 |
| EP | 0 853 950 | 10/2002 |
| EP | 2 119 460 | 11/2009 |
| EP | 2848268 A1 | 3/2015 |
| GB | 488 232 | 7/1938 |
| GB | 1 415 096 | 11/1975 |
| GB | 1 549 756 | 3/1977 |
| GB | 2 195 255 A | 4/1988 |
| GB | 2 235 877 A | 3/1991 |
| GB | 2 307 180 A | 5/1997 |
| GB | 2 329 127 A | 3/1999 |
| GB | 2 336 546 A | 10/1999 |
| GB | 2 344 531 A | 6/2000 |
| GB | 2 415 908 | 1/2006 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1991 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 00/21586 | 4/2000 |

(56) References Cited

FOREIGN PATENT DOCUMENTS

| WO | WO 03/005943 | 1/2003 |
|---|---|---|
| WO | WO 03/018098 | 3/2003 |
| WO | WO 03/030966 | 4/2003 |
| WO | WO 03/045492 | 6/2003 |
| WO | WO 03/057070 | 7/2003 |
| WO | WO 03/057071 | 7/2003 |
| WO | WO 03/057307 | 7/2003 |
| WO | WO 03/086232 | 10/2003 |
| WO | WO 03/092620 | 11/2003 |
| WO | WO 03/101508 | 12/2003 |
| WO | WO 2004/018020 | 4/2004 |
| WO | WO 2005/009488 | 2/2005 |
| WO | WO 2006/015599 | 2/2006 |
| WO | WO 2006/105892 | 10/2006 |
| WO | WO 2008/020862 | 2/2008 |
| WO | WO 2008/048481 | 4/2008 |
| WO | WO 2008/141228 | 11/2008 |

OTHER PUBLICATIONS

U.S. Appl. No. 13/866,346, filed Apr. 19, 2013, Patel et al.

Bagautdinov (Kazan), "Variant of External Vacuum Aspiration in the Treatment of Purulent Diseases of Soft Tissues," UDC 616-002.36 (94-96).

Bjorn, et al., "Irrigation Treatment in Split-thickness Skin Grafting of Intractable Leg Ulcers," Scand J Plast Reconstr Surg 19: 211-213,1985.

Chardack, et al., "Experimental studies on Synthetic Substitutes for Skin and Their Use in the Treatment of Burns," vol. 155, No. 1 (128-136), 1961.

Chariker, M. E. et al. (eds), "Effective Management of Incisional and Cutaneous Fistulae with Closed Suction Wound Drainage," Contemporary Surgery, vol. 34, Jun. 1989, pp. 59-63.

Fleischmann, "Vacuum Sealing for Treatment of Problematical Wounds", University Surgical Clinic and Polyclinic- Accident Surgery Department, WundForum Spezial-IHW 94.

Fleischmann, et al., Vacuum Sealing: Indication, Technique and Results, Emr J Orthop Surg Tramatol (1995) 5:37-40.

Göran Sandén, MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Gorica Zivadinovic, et al., "Vacuum Therapy in the Treatment of Peripheral Blood Vessels," Conference Papers of the 5th Timok Medical Days, Majdanpek, 1986 (161-164).

International Search Report for PCT/US09/047137, dated Aug. 7, 2009.

International Search Report for PCT/US09/036342, dated Aug. 3, 2010.

International Search Report and Written Opinion for PCT/US2012/030829, mailed Jul. 26, 2012.

Jeter, Katherine F., et al., "Managing Draining Wounds and Fistulae: New and Established Methods", Chronic Wound Care, 1990, pp. 240-246.

Kostiuchenok, et al., "The Vacuum Effect in the Surgical Treatment of Purulent Wounds," Russian Journal: Vestnik Khirurgii, Sep. 1986, (18-21).

Meyer, MD., et al., "In Surgery, Medicine and the Specialties a Manual of its Practical Application", Bier's Hyperemic Treatment, Second Revised Edition, W.B. Saunders Company, 1909.

Mulder, GD, et al., "Clinicians' Pocket Guide to Chronic Wound Repair," Wound Healing Publications Second Edition, 1991.

Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).

Stoll, "Energetic Remedies—Cupping: Healing Within a Vacuum," https:l/www.suite101.com/article.cfm/ energetic)remedies/74531, Apr. 13, 2005.

Svedman, "A Dressing Allowing Continuous Treatment of a Biosurface," IRCS Medical Science: Biomedical Technology; Clinical Medicine; Surgery and Transplantation, 7, 221 (1979).

Svedman, "A Dressing System Providing Fluid Supply and Suction Drainage Used for Continuous or Intermittent Irrigation," Annals of Plastic Surgery, vol. 17, No. 2, Aug. 1986 (125-133).

Svedman, "Irrigation Treatment of Leg Ulcers," The Lancet, Sep. 3, 1983 (532-534).

Svedman, et al., "Staphylococcal Wound Infection in the Pig: Part I. Course," Annals of Plastic Surgery, vol. 23, No. 3, Sep. 1989 (212-218).

Teder, et al., "Continuous Wound Irrigation in the Pig," Journal of Investigative Surgery, vol. 3 (399-407).

Usupov, et al., "Active Wound Drainage," Russian Journal: Vestnik Khirugii, Apr. 1987, (42-45).

Yu A. Davydov, et al., "Bacteriological and Cylological Assessment of Vacuum Therapy of Purulent Wounds", Vestnik Khirurgii, Oct. 1988, (48-52).

Yu A. Davydov, et al., "Concepts for Clinical Biological Management of the Wound Process in the Treatment of Purulent Wounds Using Vacuum Therapy," Vestnik Khirugii, Feb. 1991, 132-135).

Yu A. Davydov, et al., "Vacuum Therapy in the Treatment of Purulent Lactation Mastitis," Russian Journal: Vesnik Khirurgii, Sep. 1986, (66-70).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

US 6,216,701, 04/2001, Heaton et al. (withdrawn)

US 7,186,244, 03/2007, Hunt et al. (withdrawn)

\* cited by examiner

NEGATIVE PRESSURE WOUND THERAPY DRESSING

CROSS-REFERENCE TO RELATED APPLICATIONS

This application is a U.S. National Phase of the PCT International Application No. PCT/US2012/030829, filed on Mar. 28, 2012, and which claims priority to application U.S. application Ser. No. 13/079,298, filed on Apr. 4, 2011.

BACKGROUND

1. Technical Field

The present disclosure relates generally to wound dressings for use in a negative pressure wound therapy (NPWT) system. In particular, the disclosure relates to a composite wound dressing that includes a wound filler or packing member affixed to a cover layer to facilitate wound healing and ease the application of the dressing to a wound.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound bite. Next, the body begins to repair itself in a stage of healing often referred to as the proliferate phase. This phase is characterized by the deposition of granulation tissue in the wound bed. Granulation tissue provides a base structure over which cells may migrate inwardly from the periphery to close the wound. Finally the process ends as collagen gives strength to new tissue over time often forming a scar.

One technique for promoting the natural healing process, particularly, but not exclusively during the proliferate phase, is known as negative pressure wound therapy (NPWT). Application of a reduced pressure, e.g. sub-atmospheric, to a localized reservoir over a wound has been found to assist in closing the wound. The reduced pressure may be effective to promote blood flow to the area, to stimulate the formation of granulation tissue and the migration of healthy tissue over the wound by the natural process. Also a reduced pressure may inhibit bacterial growth by assisting in removing fluids exuding from the wound. This technique has proven effective for chronic or non-healing wounds, but has also been used for other purposes such as post-operative wound care.

The general NPWT protocol provides for the introduction of a filler or packing member into the wound, and subsequently applying a cover layer over wound and packing member. The packing member serves to support the cover layer and also to absorb and/or promote fluid transport away from the wound bed. The wound filler may comprise such materials as non-reticulated foams, non-woven fabrics, continuous fibers or gauze. The cover layer may comprise a thin polymeric film that includes an adhesive periphery for forming a substantially fluid tight seal with the healthy skin surrounding the wound. The cover layer thus defines a vacuum reservoir over the wound where a reduced pressure may be maintained over time by the application of individual or cyclic evacuation procedures.

In some instances, applying a packing member and a cover layer individually to a wound may be a time consuming, and labor intensive process. A composite wound dressing that includes a packing member affixed to a cover layer may facilitate the application of the wound dressing to a wound for use in a (NPWT) system.

SUMMARY

The present disclosure describes a wound dressing suitable for use in negative pressure wound therapy system. The dressing includes a cover layer adapted to establish a reservoir over a wound in which a negative pressure may be maintained. The cover layer includes an opening therein through which atmospheric gasses and wound exudates may pass through the cover layer. A vacuum port is affixed to the cover layer, and establishes a substantially fluid tight seal about the opening in the cover layer. The vacuum port includes a hollow interior in fluid communication with the opening, and a connector to facilitate connection to a vacuum source. A packing member is affixed to the cover layer. The packing member is adapted to fill the wound and to support the cover layer when a negative pressure is applied to the reservoir.

The packing member may include an open-celled foam arranged to exhibit a generally planar cross-section, and may radially surround the vacuum port. The packing member may be spirally arranged and include a spirally-shaped major seam separating individual windings of spiral. The packing member may also include a plurality of minor seams extending laterally across the individual windings of the spiral to define discrete and separable components of the packing member.

The packing member may alternatively include a plurality of discrete elongated fingers extending distally from a distal side of the cover layer. The elongated fingers may be constructed of a tow of continuous filaments, or the elongated fingers may be constructed of strips of a foam material. The packing member may also include a supporting media affixed to the cover layer that defines a plurality of apertures therein through which a proximal end of the elongated fingers are interlaced. The supporting media may be constructed as a generally planar polymeric mesh. The supporting media may also define a flange of the vacuum port, or the supporting media may include a relatively pliable portion of a flange of the vacuum port.

The packing member may include a cellulose solution that is adapted to maintain the packing member in a relatively rigid condition prior to installation of the wound dressing, and a relatively pliable condition when the packing member is in contact with a wound. The cellulose solution may be arranged on an outer surface of the elongated fingers to substantially encapsulate the elongated fingers, allowing the clinician to strategically place the wound filler material in the wound bed without interfering with the application of the adhesive layer. The cellulose solution may be infused with vitamins and minerals that promote healthy wound healing, such as vitamin E.

According to another aspect of the disclosure, a wound dressing includes a cover layer adapted to establish a reservoir over a wound in which a negative pressure may be maintained. The cover layer includes an opening therein through which atmospheric gasses and wound exudates may pass through the cover layer. A vacuum port is affixed to the cover layer, and establishes a substantially fluid tight seal about the opening in the cover layer. The vacuum port includes a hollow interior in fluid communication with the opening, and a connector to facilitate connection to a vacuum source. A packing member is permanently affixed to a distal side of the cover layer, and includes a plurality of discrete elongated fingers extending distally from the distal side of the cover layer.

The cover layer may include an adhesive coating on the distal side thereof, and an adhesive bond may be established between the cover layer and the packing member by the adhesive coating. A release sheet or liner may be affixed to the cover layer by the adhesive coating on the distal side of the cover layer such that the packing member is interposed between the release sheet and the cover layer. The packing member may include a polymeric foam material cut such that each of the elongated fingers extends from continuous portion of the foam material. In some embodiments, the elongated fingers of the packing member may extend through an opening in the release liner.

According to another aspect of the present disclosure, a system for negative or subatmospheric pressure therapy in connection with healing a wound includes a cover layer dimensioned for positioning relative to a wound bed of a subject to establish a reservoir over the wound bed in which a negative pressure may be maintained. A packing member is permanently affixed to a distal side of the cover layer, and includes a polymeric foam material. The system also includes a vacuum source in fluid communication with the wound bed.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
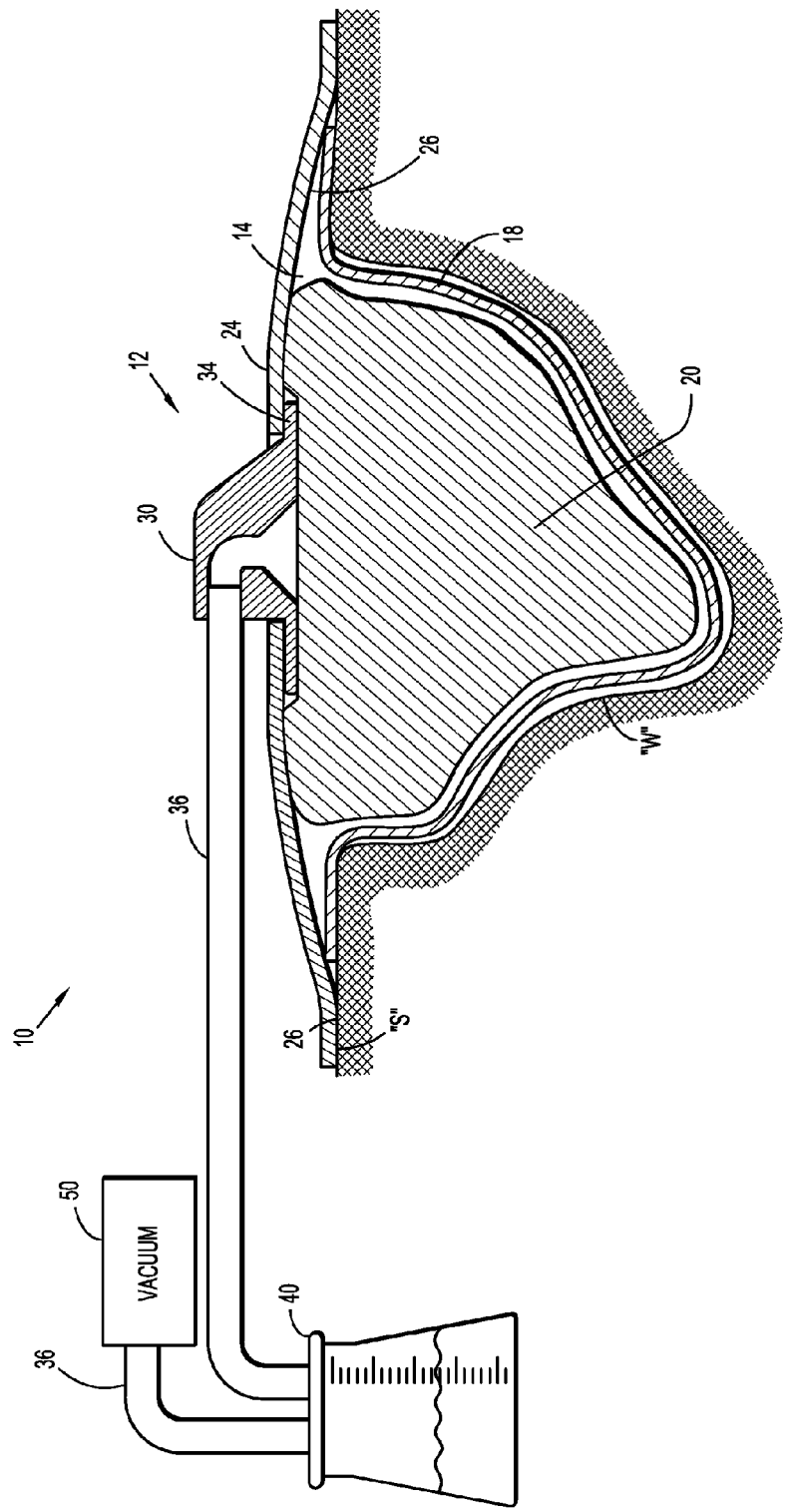
FIG. 1 is a cross-sectional view of a negative pressure wound therapy apparatus with a wound dressing installed over a wound in accordance with the present disclosure.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Referring initially to FIG. 1, an apparatus 10 for negative pressure wound therapy (NPWT) is depicted for use on a wound "w" surrounded by healthy skin "s" in accordance with the present disclosure. Apparatus 10 may be used to subject the wound "w" to a negative pressure continuously, or in varying intervals depending on the nature and severity of the wound "w." The use of a wound dressing in this manner has been found to promote healing by reducing the probability of infection, stimulating the deposition of granulation tissue and other beneficial processes. To facilitate the application of a negative pressure, the apparatus 10 includes a wound dressing 12 positioned relative to the wound "w" to define a reservoir 14 in which a negative pressure appropriate to stimulate healing may be maintained.

Wound dressing 12 includes an optional contact layer 18 positioned in direct contact with the bed of wound "w." Contact layer 18 may comprise a porous film including apertures therein permitting the negative pressure applied to the reservoir 14 to penetrate into the wound "w," and also permitting exudates to be drawn from the wound "w." Three-dimensional formed and apertured films such as those provided by Tredegar Film Products of Richmond, Va., may be suitable for constructing contact layer 18.

Packing member 20 is positioned in the wound "w" over the contact layer 18 and is intended to allow wound dressing 12 to absorb and capture wound exudates, or to transport wound exudates away from the wound "w" and out of the dressing 12. Packing member 20 is shaped to be conformable to the shape of wound "w," and to slightly overfill the wound "w." Alternatively, the packing member 20 may be sized and shaped to fill the wound "w" up to the level of healthy skin "s."

The packing member 20 may be constructed of an absorbent material such as gauze, reticulated foam, continuous fibers or alginate fibers to receive or transport any exudate that migrates through the contact layer 18. One particular antimicrobial dressing, commercially available under the trademark Covidien™ AMD offered by Tyco Healthcare Group LP (d/b/a Covidien), may be suitable for use as packing member 20. The Covidien™ AMD Foam dressing is polyurethane-based foam including the antiseptic agent polyhexamethylene biguanide (PHMB). A microstructured open-celled surface on the foam pad promotes absorption of exudates, and the added PHMB attacks bacteria on and within the dressing 12. The Covidien™ AMD Foam dressing is described in greater detailed below with reference to FIG. 2.

To discourage adhesion to the wound "w," the packing member 20 may also comprise a material configured such that any stray fibers do not tend to protrude through apertures formed in contact layer 18 where they may become engulfed by newly forming granulation tissue. One particular type of material exhibiting this characteristic is formed of a tow of continuous filaments comprising either natural or man-made fibers. Continuous filaments include those relatively long strands of a synthetic material such as nylon, rayon, etc., which may offer a smooth continuous outer surface substantially free of the protruding fibrils commonly associated with natural materials such as cotton. The use of continuous filaments of a hydrophobic material such as polyolefin may permit a complete removal of packing member 20 when the dressing 12 is changed without re-injuring the wound "w."

Wound dressing 12 also includes a cover layer 24. Cover layer 24 is positioned over the wound "w" such that an adhesive 26 on an underside of the cover layer 24 forms a substantially fluid-tight seal with the surrounding skin "s." Thus, cover layer 24 may act as both a microbial barrier to prevent contaminants from entering the wound "w," and also a fluid barrier to maintain the integrity of vacuum reservoir 14. The adhesive 26 on the underside of the cover layer 24 also affixes the packing member 20 to the cover layer 24. Thus, the cover layer 24 and the packing member 20 may be installed on over the wound "w" together as a single component.

Cover layer 24 is preferably formed from a moisture vapor permeable membrane to promote the exchange of oxygen and moisture between the wound "w" and the atmosphere, and is preferably transparent permit a visual assessment of wound conditions without requiring removal of the cover layer 24. A transparent polyurethane membrane providing a sufficient moisture vapor transmission rate (MVTR) for use as cover layer 24 is sold under the trade name POLYSKIN®II by Tyco Healthcare Group LP (d/b/a Covidien). Alternatively, cover layer 24 may comprise an impermeable membrane or a substantially rigid member.

An optional vacuum port 30 having a flange 34 may also be included in wound dressing 12 to facilitate connection of the wound dressing 12 to a fluid conduit 36. An upper surface of the flange 34 is adhered to the cover layer 24 by the adhesive 26 on the underside of the cover layer 24. Thus, the vacuum port 30 is affixed to the cover layer 24, and may be installed over the wound "w" together with the cover layer 24 and the packing member 20 as a single component. Alternatively, an adhesive (not shown) on the underside the flange 34 may be provided such that the vacuum port 30 may be installed over the cover layer 24. Vacuum port 30 may be provided as a pre-affixed component of dressing 12, as a component of fluid conduit 36 or entirely independently. Alternatively, vacuum port 30 may be eliminated from dressing 12 if other provisions are made for providing fluid communication with the fluid conduit 36.

The vacuum port 30 may be constructed of a polypropylene material and may be configured as a rigid or flexible, low-profile component. The vacuum port 30 may be adapted to receive fluid conduit 36 in a releasable and fluid-tight manner. An outer surface of the fluid conduit 36 may frictionally engage an inner surface of the vacuum port 30. Alternatively, a barbed connector (see FIG. 5), quick disconnect, bayonet coupling or permanent coupling methods may be employed to couple the fluid conduit to the vacuum port 30. A hollow interior of the vacuum port 30 provides fluid communication between the fluid conduit 36 and the reservoir 14.

Fluid conduit 36 extends from the vacuum port 30 to provide fluid communication between the reservoir 14 and a fluid collection canister 40. Any suitable conduit may be used for fluid conduit 36 including those fabricated from flexible elastomeric or polymeric materials. Fluid conduit 36 may connect to the canister 40 in a fluid-tight manner by any appropriate mechanism including any of the mechanisms described above for connecting the fluid conduit to the vacuum port 30.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NWPT apparatus 10. Vacuum source 50 may comprise a peristaltic pump, a diaphragmatic pump or other mechanism that is biocompatible and draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mmHg, more preferably, about 75 mmHg to about 125 mmHg, or more preferably, about 40 mmHg to about 80 mmHg.

Figure 2:
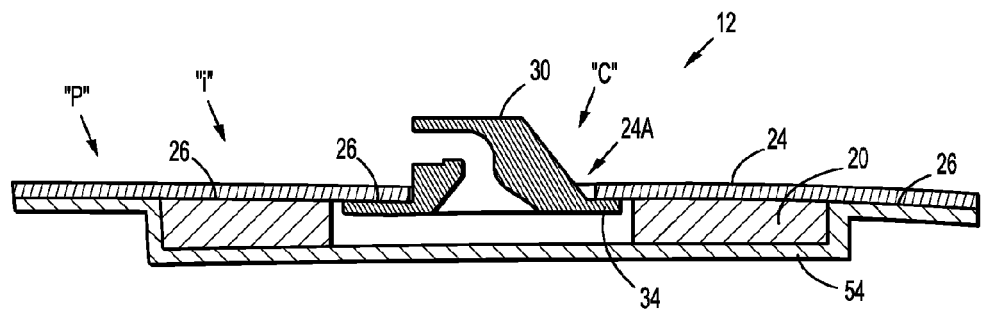
FIG. 2 is a cross-sectional view of the wound dressing of FIG. 1 as packaged prior to application over the wound.

Referring now to FIG. 2, a wound dressing 12 is depicted in an initial configuration prior to application over the wound "w" (FIG. 1). The packing member 20, cover layer 24 and the vacuum port 30 are all coupled to one another by the adhesive 26 on the underside of the cover layer 24. The vacuum port 30 extends through a central opening 24a in the cover layer 24 and is adhered to a radially central region "c" of the cover layer 24 by the flange 34. The flange 34 establishes a substantially fluid tight seal with the cover layer 24. The packing member 20 radially surrounds the vacuum port 30 and is adhered to a radially intermediate region "i" of the cover layer 24. A release liner 54 is adhered to the adhesive 26 at a peripheral region "p" of the cover layer 24 and serves to protect the adhesive 26 and the packing member 20 prior to use of the dressing 12. The release liner 54 may be constructed of a silicone coated paper or similar material that will readily detach from the cover layer 26 without inhibiting ability of the adhesive 26 in the peripheral region "p" to form a fluid-tight seal with the skin "s" (FIG. 1).

The packing member 20 depicted in FIG. 2 is constructed as a die-cut pad or disc of the Covidien™ AMD foam, and is adhered to the cover layer 24 by the adhesive 26 radially surrounding the vacuum port 30. The packing member 20 assumes a generally planar cross-section and occupies a relatively small volume prior to exposure to a moist wound environment. The planar configuration of the packing member 20 is suitable for use in wounds such as shallow ulcers that generally do not require a large amount of material to fill the wound. The tendency of the Covidien™ AMD foam to swell in the presence of moisture helps fill the void of the wound "w" (FIG. 1), and thus, provides support to the cover layer 24 as the wound "w" is subjected to negative pressure. The tendency to swell in the presence of moisture also helps to maintain intimate contact between the packing member 20 and the wound bed "w" (FIG. 1). The continuous nature of a die-cut foam pad alleviates a risk of portions of the packing member being inadvertently left in the wound "w" when the wound dressing 12 is removed. The microstructured open celled surface on the foam pad discourages ingrowth of tissue from a wound site into the matrix of the packing member 20, and thus alleviates the risk of reinjuring a wound when the wound dressing 12 is removed or changed. In other embodiments (not shown) a gauze pad or non-woven wound dressing sponge may be affixed to the distal side of the foam packing member 20.

Figure 3:
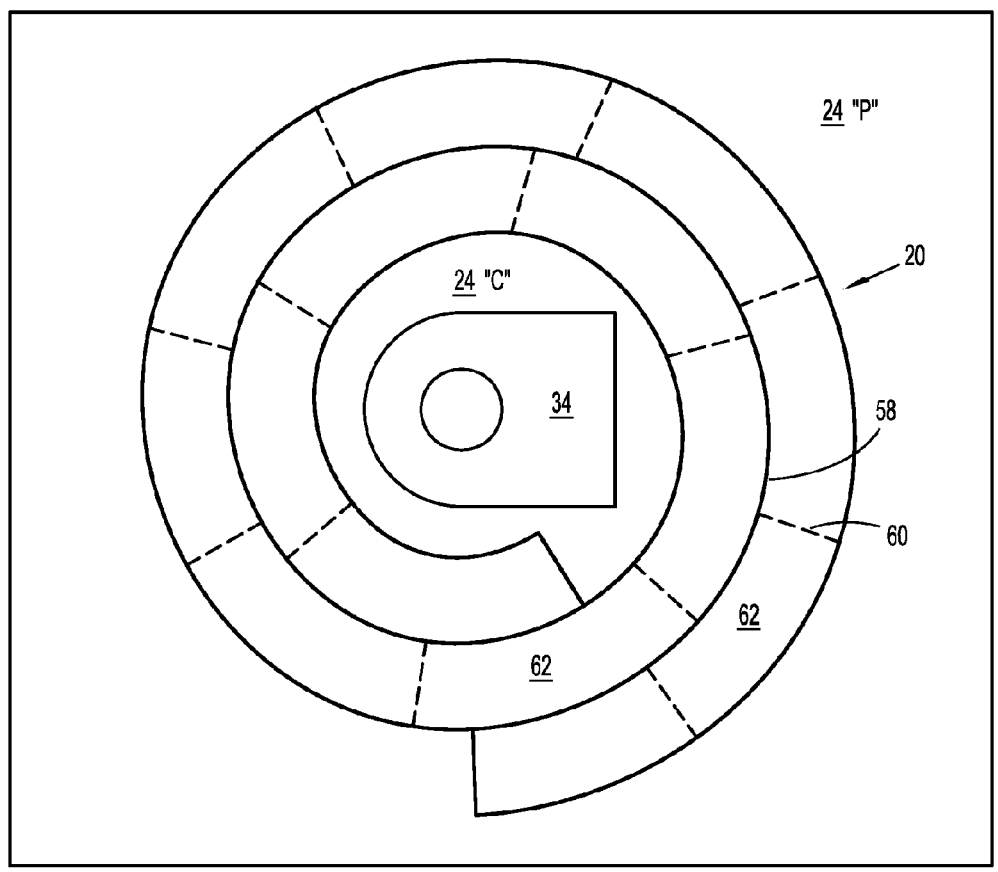
FIG. 3 is a distal or wound-facing side view of the wound dressing of FIG. 1 depicting a spiral die-cut packing member affixed to a cover layer.

Referring now to FIG. 3, the packing member 20 is die-cut to assume a spiral configuration. A spirally shaped major seam 56 is cut between successive windings or layers of the spiral, and a plurality of minor seams 60 is cut laterally into the windings of the spiral to define a plurality of discrete components 62. The seams 56, 60 may extend entirely through the packing member 20 to define the discrete separable components 62 of the spiral. Alternately, the seams 56, 60 may extend partially through the packing member 20 or may be defined by a series of perforations to permit each of the discrete components 62 to be readily separable from the spiral. Thus, a clinician may unwind the spiral and tear or cut any number of discrete components 62 from the spiral as necessary to conform the packing member 20 to the size of the wound "w."

Figure 4:
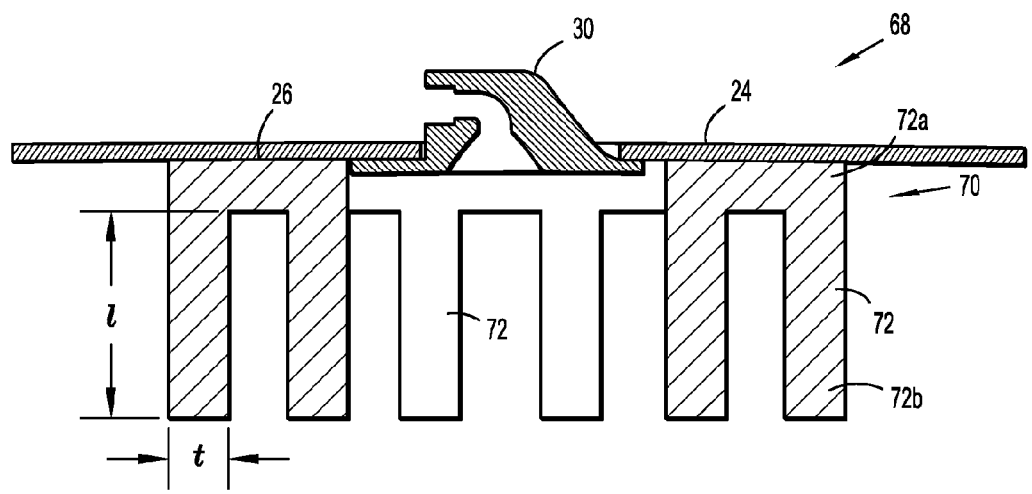
FIG. 4 is a cross-sectional view of an alternate embodiment of a wound dressing depicting a packing member cut to form elongated fingers.

Referring now to FIG. 4, an alternate embodiment of a wound dressing 68 includes a cover layer 24 and a vacuum port 30 affixed thereto in a manner substantially similar to the wound dressing 12 described above with reference to FIG. 2. The wound dressing 68 also includes a packing member 70 affixed to the distal side of the cover layer 24. The packing member 70 includes a plurality of elongated fingers 72 that may be cut to an appropriate size or length at the time the wound dressing 68 is installed to accommodate a particular wound configuration. The packing member 70 may be constructed of any of the materials discussed above for construction of the packing member 20 (FIG. 2) including a tow of continuous filaments, and a die-cut open celled foam having fingers 72 cut therein.

Each of the elongated fingers includes a proximal end 72*a* affixed to the cover layer 24, and a free end 72*b* extending therefrom in a distal direction. Where the packing member 70 is constructed of a foam material, the elongated fingers 72 may have a length "l" in the range of about 1 inch to about 4 inches, and a thickness "t" in the range of about 0.125 inches to about 0.5 inches. In other embodiments, where the packing member 70 is constructed of a tow of continuous filaments, the elongated fingers 72 may be substantially longer and narrower. The fingers 72 are supported by the adhesive 26 on the distal side of the cover layer, and may hang down from the cover layer 24 into the wound "w" when as the dressing 12 is installed.

Figure 5:
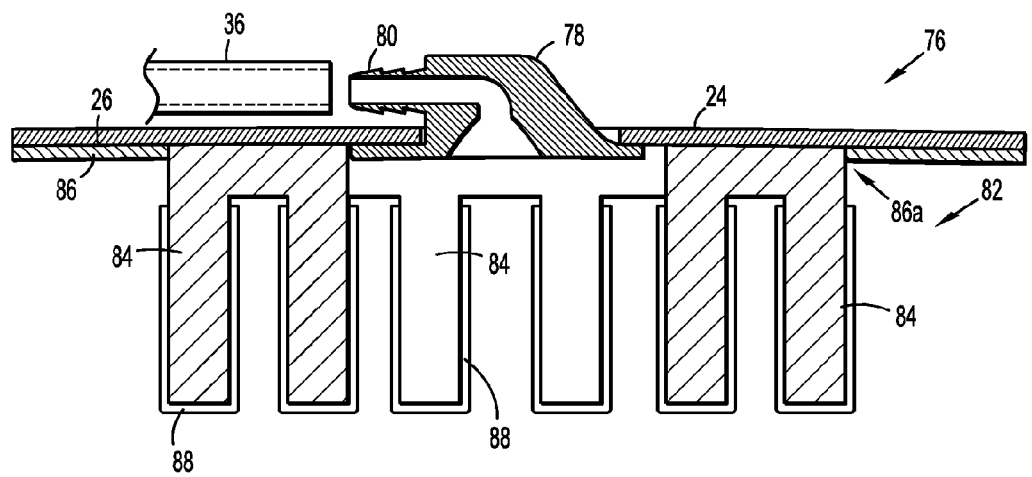
FIG. 5 is a cross-sectional view of an another alternate embodiment of a wound dressing the wound dressing including elongated fingers encapsulated in a thin shell.

Referring now to FIG. 5, an alternate embodiment of a wound dressing 76 includes a cover layer 24 and a vacuum port 78 affixed thereto. The vacuum port 78 includes a barbed connector 80 for engaging an interior surface of a tubing section 36 in a fluid-tight manner. In other embodiments (not shown) the tubing section 36 and vacuum port 78 may the provided or fitted with a universal connector. A universal connector is a connector of a type used to interchangeably connect a variety of different components to one another, as opposed to a propriety connector used to connect only a specific component to another specific component. A universal connector may, for example, employ an industry standard connector type, such that the dressing 76 may be used in conjunction with a wide variety of standard medical equipment.

The wound dressing 76 includes a packing member 82 affixed to the distal side of the cover layer 24, and the packing member 82 includes a plurality of elongated fingers 84 extending in a distal direction from the cover layer 24 in a manner substantially similar to the elongated fingers 72 described above with reference to FIG. 4. The elongated fingers 84 could also be constructed of a continuous tow treated with PHMB for microbial efficacy. The wound dressing 76 includes a release sheet or liner 86 adhered to the adhesive 26 of the cover layer 24, and the release liner 86 includes an opening 86*a* therein through which the packing member 82 and the elongated fingers 84 extend. The opening 86*a* in the release liner 86 permits a substantially flat release liner 86 to protect the adhesive 26 prior to use of the dressing 76, and may facilitate application of the release liner 86 to the cover layer 24 during manufacturing of the dressing 76.

The elongated fingers 84 are each encapsulated in a thin shell 88 disposed on an exterior surface of the respective finger 84. The shell 88 is constructed of a cellulose solution that may contain proteins and vitamins that could aid in the wound healing process. The cellulose serves as a stiffening agent that provides some rigidity to the fingers 84 to facilitate handling and placement of the wound dressing 76. Once the fingers are wetted by the moist wound environment, the fingers 84 will transition to a soft and pliable configuration that promotes patient comfort. In other configurations, the shell 88 could be constructed of a polymeric material having a glass transition temperature above room temperature (i.e., above about 25° C.), but below body temperature (i.e., below about 37° C.). At room temperature, the coating stiffens the fingers 84 for ease in handling and manipulation, and upon placement in a wound "w," the shell 88 will soften as the temperature rises above the glass transition temperature of the polymeric material, thereby rendering the fingers pliable so that they conform to the contours of the wound "w." In still other configurations, the fingers 84 may be soaked in the cellulose solution or polymeric material such that the stiffening agent is absorbed into the matrix of the fingers 84 rather than being disposed on an exterior surface as shell or coating.

Figure 6:
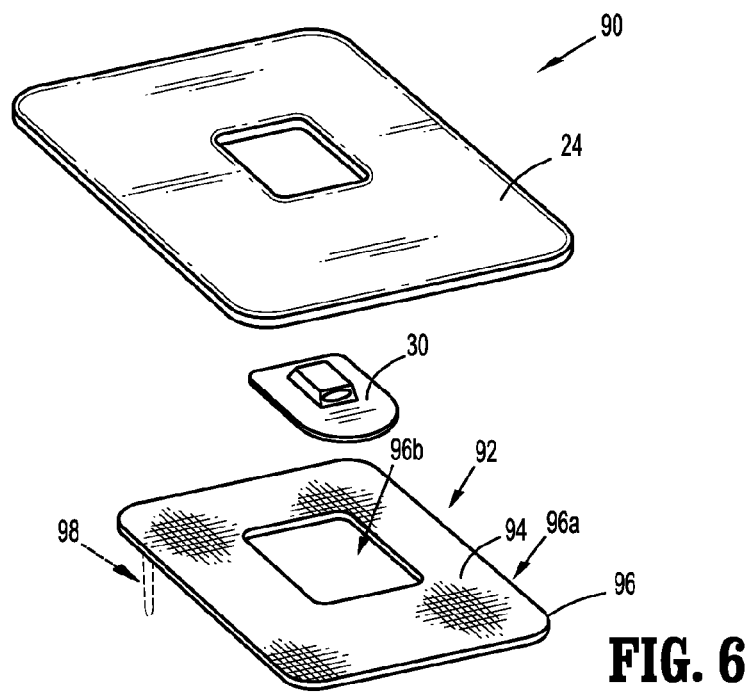
FIG. 6 is an exploded, perspective view of an alternate embodiment of a wound dressing including a packing member woven into a supporting media.

Referring now to FIG. 6, an alternate embodiment of a wound dressing 90 includes a cover layer 24 and a vacuum port 30 substantially similar to the cover layer 24 and vacuum port 30 of wound dressing 12 described above with reference to FIG. 2. The wound dressing 90 also includes a packing member 92 that may be affixed to the distal side of cover layer 24 such that the entire wound dressing 90 may be applied over the wound "w" (FIG. 1) as a single component. The packing member 92 is constructed of a continuous tow 94 woven into a supporting media 96. The supporting media 96 is constructed as a generally planar, polypropylene screen or mesh including apertures 96*a* therein that are sized and shaped to accommodate the tow 94 interlaced therethrough. A central opening 96*b* is defined through the supporting media 96 that is sized to accommodate the vacuum port 30. The packing member 92 may thus be affixed to the cover layer 24 to radially surround the vacuum port 30. The tow 94 may be woven closely to the supporting media 96 such that the packing member 92 defines a substantially flat pad, or alternatively, the tow 94 may be arranged to protrude or hang in a distal direction from the supporting media 96 such that the tow 94 defines elongated fingers 98 as depicted in phantom. In other embodiments (not shown) the supporting media 96 may be configured to receive thin strips of a foam material, woven medical fabrics, or non-woven material woven therethrough.

Figure 7:
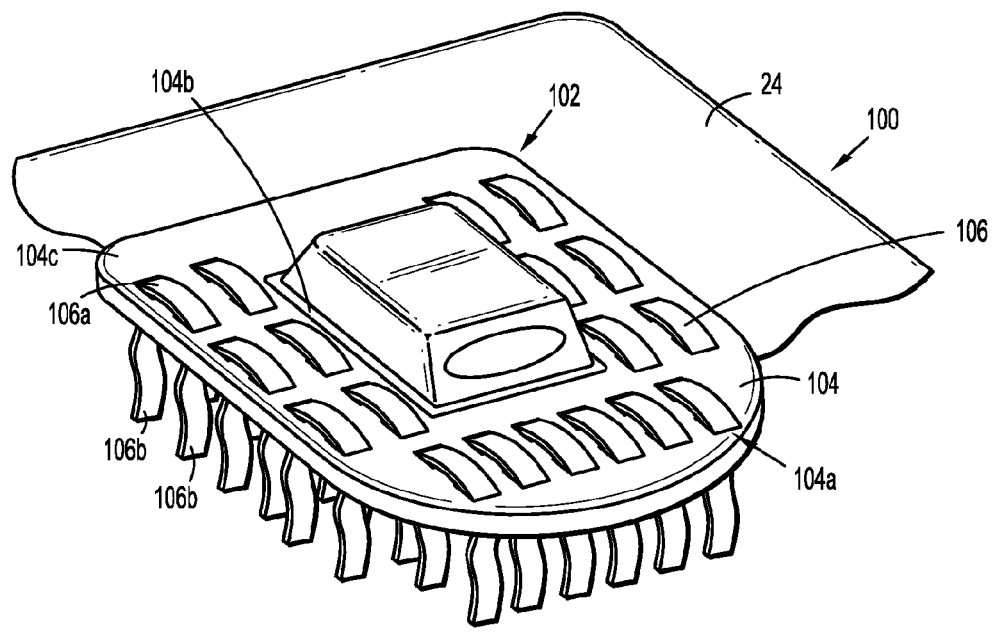
FIG. 7 is a partial, perspective view of an alternate embodiment of a wound dressing including a port member including a flange serving as a supporting media for a packing member.

Referring now to FIG. 7, an alternate embodiment of a wound dressing 100 includes a cover layer 24 and a vacuum port 102 affixed thereto. The vacuum port 102 includes a flange 104 that serves to affix the vacuum port 102 to the cover layer 24 in a substantially fluid-tight manner, and also serves to provide a supporting media for thin strips of a foam material 106. The strips 106 include a proximal end 106*a* interlaced through apertures 104*a* defined in the flange 104, and a pair of free ends 106*b* extending from the flange 104 in a distal direction. The free ends 106*b* may be cut to an appropriate length at the time of application to a wound "w" (FIG. 1).

In some embodiments, a central portion 104*b* of the flange 104 may be constructed to exhibit a relative rigidity with respect to a radial extension 104*c* of the flange 104, which is constructed to exhibit a relatively pliability. The relatively pliable extension 104*c* may flex and bend with the cover layer 24 during evacuation cycles and promote patient comfort. The extension 104*c* may be constructed of a more pliable material than the central portion 104*b*, or alternatively, the extension 104*c* may be constructed with a tapering or reduced thickness with respect to the central portion 104*b*.

Although the foregoing disclosure has been described in some detail by way of illustration and example, for purposes of clarity or understanding, it will be obvious that certain changes and modifications may be practiced within the scope of the appended claims.

What is claimed is:

1. A wound treatment apparatus, comprising:
  a cover layer adapted to establish a reservoir over a wound in which a negative pressure may be maintained, the cover layer including an opening therein through which atmospheric gasses and wound exudates may pass through the cover layer;

a vacuum port affixed to the cover layer to establish a substantially fluid tight seal about the opening in the cover layer, the vacuum port including a hollow interior in fluid communication with the opening in the cover layer, and a connector to facilitate connection to a vacuum source; and a packing member adapted to fill the wound and to support the cover layer when a negative pressure is applied to the reservoir, the packing member comprising a plurality of rows of parallel discrete elongated fingers, the discrete elongated fingers extending distally from a distal side of the cover layer, wherein each elongated finger comprises a continuous strip of open-celled foam with no inner conduit, and wherein the plurality of discrete elongated fingers are separated from one another by a plurality of gaps.

2. The wound treatment apparatus according to claim 1, further comprising a vacuum source.

3. The wound treatment apparatus according to claim 1, wherein the discrete elongated fingers are encapsulated by shells.

4. The wound treatment apparatus according to claim 1, wherein the packing member includes a supporting media affixed to the cover layer, the supporting media defining a plurality of apertures therein through which a proximal end of the elongated fingers are interlaced.

5. The wound treatment apparatus according to claim 4, wherein the supporting media is constructed as a generally planar polymeric mesh.

6. The wound treatment apparatus according to claim 4, wherein the supporting media defines a flange of the vacuum port.

7. A wound treatment apparatus, comprising:

a cover layer adapted to establish a reservoir over a wound in which a negative pressure may be maintained, the cover layer including an opening therein through which atmospheric gasses and wound exudates may pass through the cover layer;

a vacuum port affixed to the cover layer to establish a substantially fluid tight seal about the opening in the cover layer, the vacuum port including a hollow interior in fluid communication with the opening in the cover layer and a connector to facilitate connection to a vacuum source; and a packing member, the packing member including a plurality of rows of parallel discrete elongated fingers comprising an open-celled foam, the discrete elongated fingers configured to extend distally from the distal side of the cover layer and a plurality of rows of parallel discrete shells comprising a polymeric material, wherein the plurality of discrete elongated fingers are configured to be inserted within the plurality of discrete shells, and wherein the plurality of discrete shells are more rigid than the plurality of discrete elongated fingers.

8. The wound treatment apparatus according to claim 7, further comprising a vacuum source.

9. The wound treatment apparatus according to claim 7, wherein the cover layer includes an adhesive coating on the distal side thereof, and wherein an adhesive bond is established between the cover layer and the packing member by the adhesive coating.

10. The wound treatment apparatus according to claim 7, further comprising a release sheet affixed to the cover layer by the adhesive coating on the distal side of the cover layer such that the packing member is interposed between the release sheet and the cover layer.

11. The wound treatment apparatus according to claim 7, wherein the packing member comprises a polymeric foam material cut such that each of the elongated fingers extends from a continuous portion of the foam material.

12. The wound treatment apparatus according to claim 7, wherein the elongated fingers are constructed of a tow of continuous filaments.

13. The wound treatment apparatus according to claim 7, wherein the elongated fingers are constructed of strips of at least one of the group consisting of gauze, woven fabrics and non-woven absorbent materials.

14. The wound treatment apparatus according to claim 7, wherein the packing member includes a cellulose solution adapted to maintain the packing member in a relatively rigid condition prior to installation of the wound dressing, and a relatively pliable condition when the packing member is in contact with a wound.

15. The wound treatment apparatus according to claim 14, wherein the cellulose solution is arranged on an outer surface of the elongated fingers to substantially encapsulate the elongated fingers.

16. The wound treatment apparatus of claim 1, wherein the packing member comprises a foam continuous portion, the plurality of rows of parallel discrete elongated fingers extending distally from the continuous portion.

17. A wound treatment apparatus, comprising:

a cover layer adapted to establish a reservoir over a wound in which a negative pressure may be maintained, the cover layer including an opening therein through which atmospheric gasses and wound exudates may pass through the cover layer;

an apertured member comprising apertures that extend from a top to a bottom of the apertured member;

a packing member adapted to fill the wound and to support the cover layer, the packing member comprising a plurality of parallel discrete elongated fingers, the discrete elongated fingers extending distally toward the wound, wherein the elongated fingers comprise an open-celled foam, and wherein the plurality of discrete elongated fingers are separated from one another by a plurality of gaps; and wherein the discrete elongated fingers extend into the apertures.

18. The wound treatment apparatus of claim 17, further comprising a foam member connecting elongated fingers, the foam member resting atop the apertured member.

* * * * *